(12) United States Patent
Baker et al.

(10) Patent No.: US 10,436,815 B2
(45) Date of Patent: Oct. 8, 2019

(54) ELECTROSPRAY IMAGING AND DEPOSITION

(71) Applicant: INDIANA UNIVERSITY RESEARCH AND TECHNOLOGY CORPORATION, Indianapolis, IN (US)

(72) Inventors: Lane Baker, Bloomington, IN (US); Elizabeth Yuill, Bloomington, IN (US); Tyler Yarger, Bloomington, IN (US); Alicia Friedman, Westerville, OH (US); John Poehlman, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/752,386

(22) PCT Filed: Aug. 12, 2016

(86) PCT No.: PCT/US2016/046817
§ 371 (c)(1),
(2) Date: Feb. 13, 2018

(87) PCT Pub. No.: WO2017/030975
PCT Pub. Date: Feb. 23, 2017

(65) Prior Publication Data
US 2019/0004086 A1    Jan. 3, 2019

Related U.S. Application Data

(60) Provisional application No. 62/205,215, filed on Aug. 14, 2015.

(51) Int. Cl.
*G01Q 80/00* (2010.01)
*G01N 33/48* (2006.01)
(Continued)

(52) U.S. Cl.
CPC ............ *G01Q 80/00* (2013.01); *B05B 5/0255* (2013.01); *G01N 33/48* (2013.01); *G01Q 60/00* (2013.01)

(58) Field of Classification Search
CPC ......... B01L 2200/12; B01L 2300/0838; B01L 2300/0896; B01L 3/0275; G01N 11/00;
(Continued)

(56) References Cited

U.S. PATENT DOCUMENTS 7,824,620 B2 * 11/2010 Bau ....................... B01L 3/0275
422/501
2005/0072915 A1    4/2005 Stults et al.
(Continued)

OTHER PUBLICATIONS

Yuill et al. "Scanning Electrospray Microscopy with Nanopipets", Oct. 26, 2015, Analytical Chemistry, 2015, 87, 11182-11186 (Year: 2015).*

(Continued)

*Primary Examiner* — David A Vanore
(74) *Attorney, Agent, or Firm* — Barnes & Thornburg LLP; Scott Rothenberger; Bradford Addison

(57) ABSTRACT

Methods for imaging a substrate include: inducing an electrospray from a nanopipette probe; varying a distance between the nanopipette probe and a surface of the substrate until a predefined electrospray current and/or a predefined distance threshold is reached; and determining a topography of the surface of the substrate based on feedback derived from distance dependency of the electrospray current. Apparatuses for performing scanning electrospray microscopy and methods for spatially controlled deposition of material on surfaces of substrates are described.

20 Claims, 10 Drawing Sheets

(51) Int. Cl.
*B05B 5/025* (2006.01)
*G01Q 60/00* (2010.01)

(58) Field of Classification Search
CPC .. G01N 17/002; G01N 17/006; G01N 17/046; G01N 33/28; G01N 33/2829; G01N 33/48728; G01Q 10/00; G01Q 10/02; G01Q 10/065; G01Q 60/00; G01Q 60/44; G01Q 80/00
USPC .......................................................... 850/43
See application file for complete search history.

(56) References Cited

U.S. PATENT DOCUMENTS

| | | |
|---|---|---|
| 2006/0115971 A1 | 6/2006 | Bau et al. |
| 2009/0152371 A1 | 6/2009 | Stark et al. |
| 2009/0207615 A1* | 8/2009 | Frick .................. F21L 4/045 362/279 |
| 2009/0260114 A1 | 10/2009 | Korchev et al. |
| 2011/0131690 A1* | 6/2011 | Novak .................. B82Y 35/00 850/43 |
| 2016/0169790 A1* | 6/2016 | Bennis ................. G01N 17/002 73/114.77 |

OTHER PUBLICATIONS

Cheng, Y.T., et al. "Effects of Micro-and Nano-Structures on the Self-Cleaning Behaviour of Lotus Leaves", Nanotechnology 17 (2006) pp. 1359-1362.

Eyring, C.F., et al. "Fields Currents from Points", Phys. Rev., Mar. 1928, vol. 31, pp. 900-909.

Ito, S., et al. "Volume Control of Metal-Plating Deposition Using a Nanopipette Probe by Controlling Electric Charge", Japanese J. of Appl. Phys., 49 (2010), 08LB16-1, 5 pages.

Iwata, F., et al. "Nanometre-Scale Deposition of Colloidal Au Particles Using Electrophoresis in a Nanopipette Probe", Nanotechnology 18 (2007) 105301, 5 pages.

Jones, R., et al. "The Production of Charged Monodisperse Fuel Droplets by Electric Dispersion", J. Phys. D: Appl. Phys., 1971, 4, pp. 1159-1166.

Kameoka, J., et al. "A Scanning Tip Electrospinning Source for Deposition of Oriented Nanofibres", Nanotechnology 14(2003), pp. 1124-1129.

Kim, K., et al. "Drop-on-Demand Patterning of Bacterial Cells Using Pulsed Jet Electrospraying", Anal. Chem., vol. 82, No. 5, Mar. 1, 2010, pp. 2109-2112.

Moerman, R., et al. "Miniaturized Electrospraying as a Technique for the Productions of Microarrays of Reproducible Micrometer-Sized Protein Spots", Anal. Chem., vol. 73, No. 10, May 15, 2001, pp. 2183-2189.

Morozov, V.N., et al. "Electrospray Deposition as a Method for Mass Fabrication of Mono- and Multicomponent Microarrays of Biological and Biologically Active Substances", Anal. Chem., 1999, 71, pp. 3110-3117.

Pfeifer, R.J., et al. "Parametric Studies of Electrohydrodynamic Spraying", AIAA Journal, Mar. 1968, vol. 6, No. 3, pp. 496-502.

Smith, D., "The Electrohydrodynamic Atomization of Liquids", IEEE Trans. Ind. Appl., 1986, vol. IA-22, No. 3, pp. 527-535.

Ushiki, T., et al. "Scanning Ion Conductance Microscopy for Imaging Biological Samples in Liquid: A Comparative Study with Atomic Force Microscopy and Scanning Electron Microscopy", Micron 43 (2012), pp. 1390-1398.

Wong, T., et al. "Dependence of Macroscopic Welling on Nanoscopic Surface Textures", Langmuir 20098, 25 (22), pp. 12851-12854.

Yuill, E.M., et al. "Electrospray Ionization from Nanopipette Emitters with Tip Diameters of Less than 100 NM", Anal. Chem., vol. 85, pp. 8498-8502.

PCT International Search Report and Written Opinion completed by the ISA/US on Nov. 23, 2016 and issued in connection with PCT/US2016/046817.

Liu, Bing-Chen, et al. "Scanning ion conductance microscopy: a nanotechnology for biological studies in live cells." Frontiers in Physiology, vol. 3, Jan. 2013, pp. 2.

* cited by examiner

ELECTROSPRAY IMAGING AND DEPOSITION

CROSS-REFERENCE TO RELATED APPLICATIONS

This application is a national stage entry under 35 U.S.C. § 371 of PCT International Application No. PCT/US2016/046817, filed Aug. 12, 2016, and claims the benefit under 35 U.S.C. § 119(e) of U.S. Provisional Patent Application No. 62/205,215, filed Aug. 14, 2015, the disclosures of which are expressly incorporated by reference in their entireties.

TECHNICAL FIELD

The present teachings relate generally to electrospray and, in some embodiments, to electrospray emitted from nanopipettes.

BACKGROUND

When sufficient voltage is applied to a liquid provided in an emitter (e.g., a capillary tube or pipette), a fine aerosol of the liquid may be produced. This aerosol is referred to as an electrospray. The inner diameter of conventional emitters used to disperse an electrospray is typically on the order of millimeters or microns.

SUMMARY

The scope of the present invention is defined solely by the appended claims, and is not affected to any degree by the statements within this summary.

By way of introduction, a first method for imaging a substrate in accordance with the present teachings includes: (a) inducing an electrospray from a nanopipette probe; (b) varying a distance between the nanopipette probe and a surface of the substrate until a predefined electrospray current and/or a predefined distance threshold is reached; and (c) determining a topography of the surface of the substrate based on feedback derived from distance dependency of the electrospray current.

A second method in accordance with the present teachings includes: (a) inducing an electrospray from a nanopipette probe, wherein an inner diameter of a tip of the nanopipette probe is less than about 300 nm; (b) scanning the substrate with the nanopipette probe at each of a plurality of lateral points relative to the surface of the substrate; (c) decreasing distance between the nanopipette probe and the surface of the substrate until a predefined electrospray current threshold is reached; (d) recording a position of the nanopipette probe when the predefined electrospray current threshold is reached at the respective point; and (e) determining a topography of the surface of the substrate based on feedback derived from distance dependency of electrospray current.

An apparatus for performing scanning electrospray microscopy in accordance with the present teachings includes (a) a nanopipette probe movably mounted relative to a surface of a substrate, wherein the nanopipette probe is configured to emit an electrospray; (b) an electrode provided in the nanopipette probe; (c) a counter-electrode provided on or proximal to the surface of the substrate; (d) a power source configured to induce a potential between the electrode and the surface sufficient to induce an electrospray directed towards the surface of the substrate; (e) a current monitoring unit configured to measure an electrospray current; and (f) a computer processor coupled to a non-transitory memory, wherein the computer processor is operative to execute computer program instructions to cause the processor to determine a topography of the surface of the substrate based on feedback derived from distance dependency of electrospray current.

A method for spatially controlled deposition of material on a surface of a substrate in accordance with the present teachings includes: (a) introducing the material into a nanopipette probe; (b) inducing an electrospray from the nanopipette probe, wherein the electrospray comprises the material; and (c) decreasing a distance between the nanopipette probe and the surface of the substrate until a predefined electrospray current and/or a predefined distance threshold is reached at the surface of the substrate.

Additional illustrative and non-limiting embodiments of the invention are described in the following enumerated clauses. All combinations of the following clauses are understood to be additional embodiments of the invention described herein. All applicable combinations of these embodiments with the embodiments described in the DETAILED DESCRIPTION section of the application are also embodiments of the invention.

1. A method for imaging a substrate, the method comprising:
    inducing an electrospray from a nanopipette probe;
    varying a distance between the nanopipette probe and a surface of the substrate until a predefined electrospray current and/or a predefined distance threshold is reached; and
    determining a topography of the surface of the substrate based on feedback derived from distance dependency of the electrospray current.

2. The method of clause 1 wherein the predefined electrospray current is less than 15 nA.

3. The method of clause 1 or 2 wherein the predefined electrospray current is less than 10 nA.

4. The method any one of the preceding clauses wherein the predefined distance is less than 10 µm.

5. The method of any one of the preceding clauses wherein the electrospray current increases as the distance decreases.

6. The method of any one of the preceding clauses wherein an inner diameter of a tip of the nanopipette probe is less than about 300 nm.

7. The method of any one of the preceding clauses wherein an inner diameter of a tip of the nanopipette probe is between about 15 nm and about 250 nm.

8. The method of any one of the preceding clauses wherein the inducing comprises:
    providing a conductive liquid in the nanopipette; and
    applying a potential between the conductive liquid and the substrate.

9. The method of clause 8 wherein the potential is large enough to induce the electrospray.

10. The method of clause 8 or 9 wherein the potential is from about 70 V to about 130 V.

11. The method of any one of clauses 8 to 10 wherein the conductive liquid comprises an electrolyte solution, a charged monomer solution, or a combination thereof.

12. The method of any one of the preceding clauses wherein at least a portion of the substrate is conductive.

13. The method of any one of the preceding clauses wherein the substrate is insulative and proximal to a conductive material.

14. The method of any one of the preceding clauses further comprising recording a position of the nanopipette probe when the predefined electrospray current is reached.

15. The method of any one of the preceding clauses further comprising:

recording a position of the nanopipette probe when the predefined electrospray current is reached;

retracting the nanopipette probe after the predefined electrospray current is reached;

advancing the nanopipette probe to a different lateral position relative to the surface of the substrate; and repeating the varying and the recording at the different lateral position.

16. A method for imaging a substrate via scanning electrospray microscopy, the method comprising:

inducing an electrospray from a nanopipette probe, wherein an inner diameter of a tip of the nanopipette probe is less than about 300 nm;

scanning the substrate with the nanopipette probe at each of a plurality of lateral points relative to a surface of the substrate;

decreasing distance between the nanopipette probe and the surface of the substrate until a predefined electrospray current threshold is reached;

recording a position of the nanopipette probe when the predefined electrospray current threshold is reached; and determining a topography of the surface of the substrate based on feedback derived from distance dependency of electrospray current.

17. An apparatus for performing scanning electrospray microscopy, the apparatus comprising:

a nanopipette probe movably mounted relative to a surface of a substrate, wherein the nanopipette probe is configured to emit an electrospray;

an electrode provided in the nanopipette probe;

a counter-electrode provided on or proximal to the surface of the substrate;

a power source configured to induce a potential between the electrode and the surface sufficient to induce an electrospray directed towards the surface of the substrate;

a current monitoring unit configured to measure an electrospray current; and a computer processor coupled to a non-transitory memory, wherein the computer processor is operative to execute computer program instructions to cause the processor to determine a topography of the surface of the substrate based on feedback derived from distance dependency of electrospray current.

18. The apparatus of clause 17 further comprising:

a piezoelectric motor configured to raise, lower, and/or laterally translate a position of the nanopipette probe relative to the surface of the substrate.

19. The apparatus of clause 17 or 18 further comprising:

a conductive liquid provided in an interior of the nanopipette probe in contact with the electrode.

20. The apparatus of any one of clauses 17 to 19 wherein the conductive liquid comprises an electrolyte solution, a charged monomer solution, or a combination thereof.

21. A method for spatially controlled deposition of material on a surface of a substrate, the method comprising:

introducing the material into a nanopipette;

inducing an electrospray from the nanopipette, wherein the electrospray comprises the material; and decreasing a distance between the nanopipette and the surface of the substrate until a predefined electrospray current and/or a predefined distance threshold is reached at the surface of the substrate.

22. The method of clause 21 wherein the predefined electrospray current is less than 15 nA.

23. The method of clause 21 or 22 wherein the predefined electrospray current is less than 10 nA.

24. The method any one of clauses 21 to 23 wherein the predefined distance is less than 10 µm.

25. The method of any one of clauses 21 to 24 wherein the electrospray current increases as the distance decreases.

26. The method of any one of clauses 21 to 25 wherein an inner diameter of a tip of the nanopipette probe is less than about 300 nm.

27. The method of any one of clauses 21 to 26 wherein an inner diameter of a tip of the nanopipette probe is between about 15 nm and about 250 nm.

28. The method of any one of clauses 21 to 27 wherein the inducing comprises:

providing a conductive liquid in the nanopipette; and applying a potential between the conductive liquid and the substrate.

29. The method of clause 28 wherein the potential is large enough to induce the electrospray.

30. The method of clause 28 or 29 wherein the potential is from about 70 V to about 130 V 31. The method of any one of clauses 28 to 30 wherein the conductive liquid comprises an electrolyte solution, a charged monomer solution, or a combination thereof.

32. The method of any one of clauses 21 to 31 wherein at least a portion of the substrate is conductive.

33. The method of any one of clauses 21 to 32 wherein the substrate is insulative and proximal to a conductive material.

34. The method of any one of clauses 21 to 33 wherein the material comprises a biomaterial, a polymer, a metal, or an etching agent.

35. The method of any one of clauses 21 to 34 further comprising controlling an amount of the material deposited on the surface of the substrate through a rate of the decreasing and/or an amount of potential applied to induce the electrospray.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 6a shows a scanning electron microscopy (SEM) image of salt deposits over a 75 µm×75 µm area at 8×8 pixels from a nanopipette having an inner diameter of about 25 nm.

FIG. 6b shows a zoomed-in image of the salt deposits shown in FIG. 6a. FIG. 6c shows x-ray photoelectron spectroscopy (XPS) spectra corresponding to the area off (red, top) and on (blue, bottom) the area imaged in FIG. 6A. The spectra have been offset by 3000 c/s for clarity.

DETAILED DESCRIPTION

In accordance with the present teachings, the distance-dependence of the electrospray process may be used to realize a new form of scanning probe microscopy referred to herein as scanning electrospray microscopy (SESM). In SESM, a nanopipette (e.g., a capillary pulled to nanoscale tip dimensions) may be used as a scanning electrode. Electrospray is generated from the nanopipette by applying suitable potential to a conductive solution (e.g., an electrolyte solution) inside of the nanopipette. The magnitude of electrospray current thus generated may be used to control or determine the distance between the probe and a surface of a substrate. In some embodiments, as further described below, the technique of SESM may be used to provide an ambient, non-contact method to investigate surface topography using the distance-dependence of electrospray current as feedback for imaging. In other embodiments, electrospray emitted from nanopipettes in accordance with the present teachings may be used to deposit materials on the surface of a substrate in a spatially controlled manner.

Figure 1:
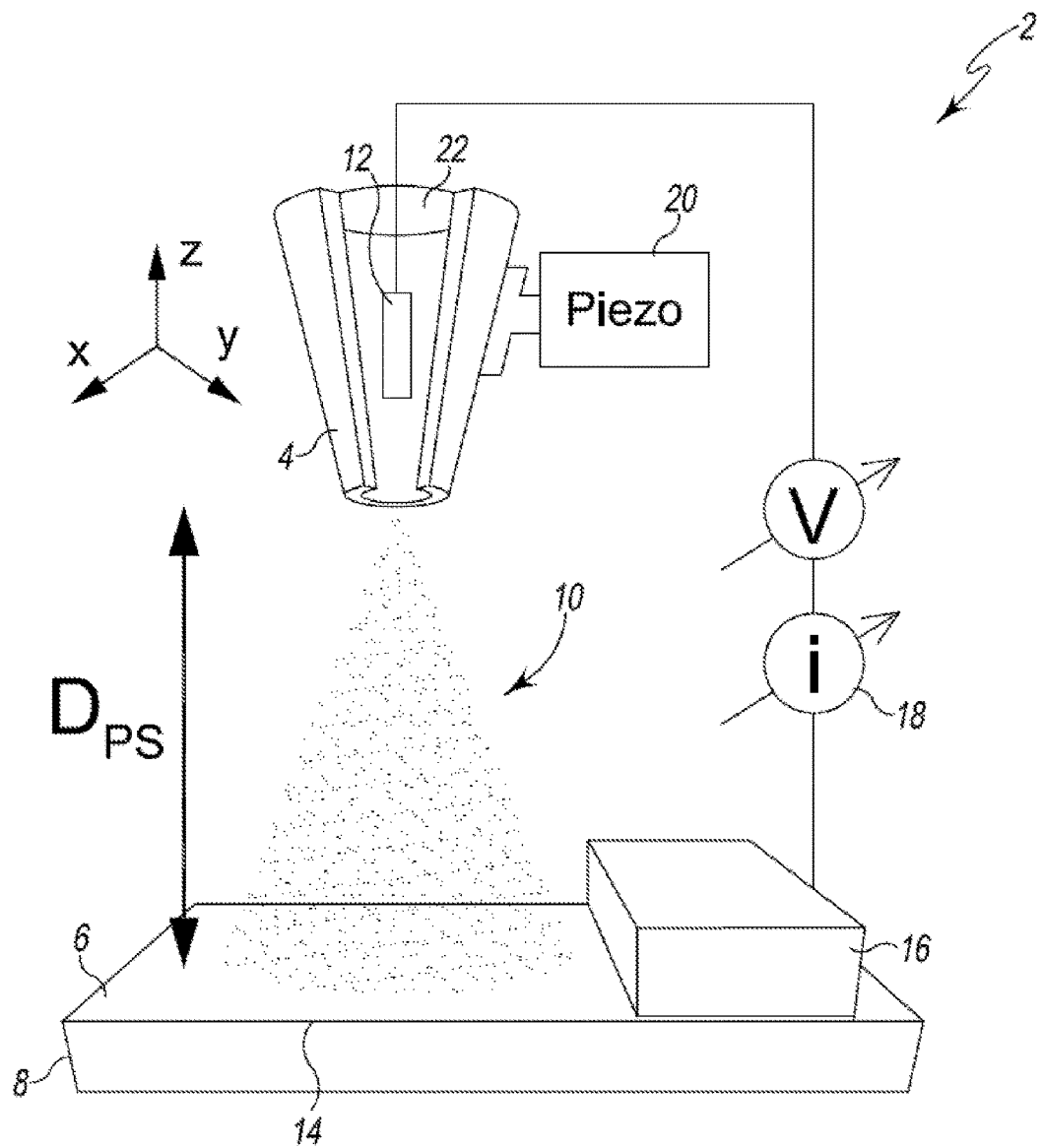
FIG. 1 shows a schematic illustration of a representative scanning electrospray microscopy (SESM) apparatus.

A general instrumental setup for scanning electrospray microscopy in accordance with the present teachings is shown in FIG. 1. An apparatus 2 for performing scanning electrospray microscopy includes a nanopipette probe 4 movably mounted relative to a surface 6 of a substrate 8. The nanopipette probe 4 is configured to emit an electrospray 10. An electrode 12 is provided in the nanopipette probe 4, and a counter-electrode 14 is provided on (or proximal to) the surface 6 of the substrate 8. The apparatus 2 further includes a power source 16 configured to induce a potential between the electrode 12 and the surface 6 sufficient to induce an electrospray 10 directed towards the surface 6 of the substrate 8. In addition, the apparatus 2 includes a current monitoring unit 18 configured to measure an electrospray current at each of a plurality of lateral points on the surface 6 of the substrate 8. A computer processor (not shown) may be used to determine a topography of the surface 6 of the substrate 8 based on feedback derived from distance dependency of electrospray current.

As shown in FIG. 1, the apparatus 2 further includes a piezoelectric motor 20 configured to raise, lower, and/or laterally translate a position of the nanopipette probe 4 relative to the surface 6 of the substrate 8. A conductive liquid 22 provided in an interior of the nanopipette probe 6 is in contact with the electrode 12. In some embodiments, the conductive liquid includes an electrolyte solution (e.g., a phosphate-buffered solution, etc.), a charged monomer solution, and/or the like, and combinations thereof.

Nanopipettes have been used as electrospray ionization-mass spectrometry (ESI-MS) emitters (E. M. Yuill, N. Sa, S. J. Ray, G. M. Hieftje and L. A. Baker, *Anal. Chem.*, 2013, 85, 8498-8502). Nanopipettes provide high signal-to-noise (S/N) and use relatively low potential to induce electrospray as compared to ESI with microscale emitters. Because electrospray depends on the electric field between the emitter and collector, the magnitude of ESI current is distance-dependent for a constant applied potential. These properties (e.g., small tips, low onset potentials, and a distance-dependent current) may be used in accordance with the present teachings to provide a new mode of feedback-controlled imaging.

While neither desiring to be bound by any particular theory nor intending to limit in any measure the scope of the appended claims or their equivalents, it is presently believed that the basis for SESM derives from the distance-dependence of electrospray current. Moreover, while neither desiring to be bound by any particular theory nor intending to limit in any measure the scope of the appended claims or their equivalents, it is presently believed that the EQNS. (1), (2), and (3) described below may be used to provide a qualitative understanding of how the distance dependence of electrospray current may provide a basis for SESM even though one or more of these equations may or may not accurately describe the actual physical phenomena involved. Nonetheless, it is to be understood that this discussion is speculative and does not in any way affect the scope of the appended claims or their equivalents.

By way of introduction, the Pfeifer and Hendricks approximation (R. J. Pfeifer and C. D. Hendricks, *AIAA J.*, 1968, 6, 496-502) shown in EQN. (1), in conjunction with the electric field-distance relationship (C. F. Eyring, S. S. MacKeown and R. A. Millikan, *Phys. Rev.*, 1928, 31, 900-909) shown in EQN. (2), may be used to understand the relationship between electrospray current, I (and also electric field, E) with the distance between the probe tip and the collecting (ground) electrode.

$$I=[(4\pi/\varepsilon)^3(9\gamma)^2\varepsilon_0^5]^{1/7}(KE)^{3/7}(V_f)^{4/7} \qquad \text{EQN. (1)}$$

Here, $\varepsilon$ is permittivity of solvent, $\gamma$ is surface tension of solvent, $\varepsilon_0$ is permittivity of a vacuum, K is conductivity of solution, $V_f$ is flow rate, and EQN. (2) is substituted for electric field.

$$E = \frac{AV}{r\ln(4d/r)} \qquad \text{EQN. (2)}$$

In EQN. (2), A is an empirical constant of 1.499 (A. R. Jones and K. C. Thong, *J. Phys. D: Appl. Phys.*, 1971, 4, 1159-1166; D. P. H. Smith, *IEEE Trans. Ind. Appl.*, 1986, IA-22, 527-535), V is the potential between the emitter tip and grounded substrate, and r is the radius of the emitter. Spraying distance, d, is distance between the emitter and substrate, or the probe-surface distance. Combination of EQNS. (1) and (2) suggests that as probe-surface distance approaches zero, spray current increases rapidly in a non-linear fashion, as shown in EQN. (3).

$$I \propto k \left[ \frac{V}{r \ln(4d/r)} \right]^{3/7} \quad (3)$$

As further explained below in reference to various Examples, the general shape of approach curves suggests electrospray currents exhibit distance-dependence suitable to serve as a feedback signal for imaging. To realize SESM, approach-retract scanning (ARS) may be used as the feedback routine for initial imaging. In ARS mode, the electrospray tip starts at a distance far from the surface and approaches until a current set point is reached. The probe position is recorded, the probe retracts, and the probe is then moved to the next pixel. Thus, each pixel in the image consists of an approach curve, which is then used to determine surface topography in a non-contact fashion.

It is to be understood that elements and features of the various representative embodiments described below may be combined in different ways to produce new embodiments that likewise fall within the scope of the present teachings.

By way of general introduction, a method for imaging a substrate in accordance with the present teachings includes: (a) inducing an electrospray from a nanopipette probe; (b) varying (e.g., increasing and/or decreasing) a distance between the nanopipette probe and a surface of the substrate until a predefined electrospray current and/or a predefined distance threshold is reached; and (c) determining a topography of the surface of the substrate based on feedback derived from distance dependency of the electrospray current.

In some embodiments, the electrospray current increases as the distance between the nanopipette probe and the surface of the substrate decreases. In some embodiments, the predetermined electrospray current threshold may be less than 15 nA, less than 14 nA, less than 13 nA, less than 12 nA, less than 11 nA, less than 10 nA, less than 9 nA, less than 8 nA, less than 7 nA, less than 6 nA, or less than 5 nA.

The inner diameter of the tip of a nanopipette probe in accordance with the present teachings may be varied based on a desired end use, as will be appreciated by one of ordinary skill. In some embodiments, the inner diameter of the tip of a nanopipette probe has nanoscalar dimensions. The inner diameter of the tip of the nanopipette probe may be one of several different values or fall within one of several different ranges. For example, it is within the scope of the present disclosure for the inner diameter of the tip of a nanopipette probe to be one of the following values: about 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, 101 nm, 102 nm, 103 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, 120 nm, 121 nm, 122 nm, 123 nm, 124 nm, 125 nm, 126 nm, 127 nm, 128 nm, 129 nm, 130 nm, 131 nm, 132 nm, 133 nm, 134 nm, 135 nm, 136 nm, 137 nm, 138 nm, 139 nm, 140 nm, 141 nm, 142 nm, 143 nm, 144 nm, 145 nm, 146 nm, 147 nm, 148 nm, 149 nm, 150 nm, 151 nm, 152 nm, 153 nm, 154 nm, 155 nm, 156 nm, 157 nm, 158 nm, 159 nm, 160 nm, 161 nm, 162 nm, 163 nm, 164 nm, 165 nm, 166 nm, 167 nm, 168 nm, 169 nm, 170 nm, 171 nm, 172 nm, 173 nm, 174 nm, 175 nm, 176 nm, 177 nm, 178 nm, 179 nm, 180 nm, 181 nm, 182 nm, 183 nm, 184 nm, 185 nm, 186 nm, 187 nm, 188 nm, 189 nm, 190 nm, 191 nm, 192 nm, 193 nm, 194 nm, 195 nm, 196 nm, 197 nm, 198 nm, 199 nm, 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, 331 nm, 332 nm, 333 nm, 334 nm, 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, 400 nm, 401 nm, 402 nm, 403 nm, 404 nm, 405 nm, 406 nm, 407 nm, 408 nm, 409 nm, 410 nm, 411 nm, 412 nm, 413 nm, 414 nm, 415 nm, 416 nm, 417 nm, 418 nm, 419 nm, 420 nm, 421 nm, 422 nm, 423 nm, 424 nm, 425 nm, 426 nm, 427 nm, 428 nm, 429 nm, 430 nm, 431 nm, 432 nm, 433 nm, 434 nm, 435 nm, 436 nm, 437 nm, 438 nm, 439 nm, 440 nm, 441 nm, 442 nm, 443 nm, 444 nm, 445 nm, 446 nm, 447 nm, 448 nm, 449 nm, 450 nm, 451 nm, 452 nm, 453 nm, 454 nm, 455 nm, 456 nm, 457 nm, 458 nm, 459 nm, 460 nm, 461 nm, 462 nm, 463 nm, 464 nm, 465 nm, 466 nm, 467 nm, 468 nm, 469 nm, 470 nm, 471 nm, 472 nm, 473 nm, 474 nm, 475 nm, 476 nm, 477 nm, 478 nm, 479 nm, 480 nm, 481 nm, 482 nm, 483 nm, 484 nm, 485 nm, 486 nm, 487 nm, 488 nm, 489 nm, 490 nm, 491 nm, 492 nm, 493 nm, 494 nm, 495 nm, 496 nm, 497 nm, 498 nm, 499 nm, or 500 nm.

It is likewise within the scope of the present disclosure for the inner diameter of the tip of a nanopipette probe to fall within one of many different ranges. In a first set of ranges, the inner diameter of the tip of a nanopipette probe is one of the following ranges: about 1 nm to 1000 nm (1µ), 2 nm to 1000 nm, 3 nm to 1000 nm, 4 nm to 1000 nm, 5 nm to 1000 nm, 6 nm to 1000 nm, 7 nm to 1000 nm, 8 nm to 1000 nm, 9 nm to 1000 nm, 10 nm to 1000 nm, 11 nm to 1000 nm, 12 nm to 1000 nm, 13 nm to 1000 nm, 14 nm to 1000 nm, 15 nm to 1000 nm, 16 nm to 1000 nm, 17 nm to 1000 nm, 18 nm to 1000 nm, 19 nm to 1000 nm, 20 nm to 1000 nm, 21 nm to 1000 nm, 22 nm to 1000 nm, 23 nm to 1000 nm, 24 nm to 1000 nm, 25 nm to 1000 nm, 26 nm to 1000 nm, 27 nm to 1000 nm, 28 nm to 1000 nm, 29 nm to 1000 nm, 30 nm to 1000 nm, 31 nm to 1000 nm, 32 nm to 1000 nm, 33 nm to 1000 nm, 34 nm to 1000 nm, 35 nm to 1000 nm, 36 nm to 1000 nm, 37 nm to 1000 nm, 38 nm to 1000 nm, 39 nm to 1000 nm, or 40 nm to 1000 nm.

In a second set of ranges, the inner diameter of the tip of a nanopipette probe is one of the following ranges: about 5 nm to 499 nm, 5 nm to 495 nm, 5 nm to 490 nm, 5 nm to 485 nm, 5 nm to 480 nm, 5 nm to 475 nm, 5 nm to 470 nm, 5 nm to 465 nm, 5 nm to 460 nm, 5 nm to 455 nm, 5 nm to 450 nm, 5 nm to 445 nm, 5 nm to 440 nm, 5 nm to 435 nm, 5 nm to 430 nm, 5 nm to 425 nm, 5 nm to 420 nm, 5 nm to 415 nm, 5 nm to 410 nm, 5 nm to 405 nm, 5 nm to 400 nm, 5 nm to 395 nm, 5 nm to 390 nm, 5 nm to 385 nm, 5 nm to 380 nm, 5 nm to 375 nm, 5 nm to 370 nm, 5 nm to 365 nm, 5 nm to 360 nm, 5 nm to 355 nm, 5 nm to 350 nm, 5 nm to 345 nm, 5 nm to 340 nm, 5 nm to 335 nm, 5 nm to 330 nm, 5 nm to 325 nm, 5 nm to 320 nm, 5 nm to 315 nm, 5 nm to 310 nm, 5 nm to 305 nm, 5 nm to 300 nm, 5 nm to 295 nm, 5 nm to 290 nm, 5 nm to 285 nm, 5 nm to 280 nm, 5 nm to 275 nm, 5 nm to 270 nm, 5 nm to 265 nm, 5 nm to 260 nm, 5 nm to 255 nm, 5 nm to 250 nm, 5 nm to 245 nm, 5 nm to 240 nm, 5 nm to 235 nm, 5 nm to 230 nm, 5 nm to 225 nm, 5 nm to 220 nm, 5 nm to 215 nm, 5 nm to 210 nm, 5 nm to 205 nm, 5 nm to 200 nm, 5 nm to 195 nm, 5 nm to 190 nm, 5 nm to 185 nm, 5 nm to 180 nm, 5 nm to 175 nm, 5 nm to 170 nm, 5 nm to 165 nm, 5 nm to 160 nm, 5 nm to 155 nm, 5 nm to 150 nm, 5 nm to 145 nm, 5 nm to 140 nm, 5 nm to 135 nm, 5 nm to 130 nm, 5 nm to 125 nm, 5 nm to 120 nm, 5 nm to 115 nm, 5 nm to 110 nm, 5 nm to 105 nm, 5 nm to 100 nm, 5 nm to 95 nm, 5 nm to 90 nm, 5 nm to 85 nm, 5 nm to 80 nm, 5 nm to 75 nm, 5 nm to 70 nm, 5 nm to 65 nm, 5 nm to 60 nm, 5 nm to 55 nm, 5 nm to 50 nm, 5 nm to 45 nm, 5 nm to 40 nm, or 5 nm to 35 nm.

In a third set of ranges, the inner diameter of the tip of a nanopipette probe is one of the following ranges: about 4 nm to 499 nm, 5 nm to 498 nm, 6 nm to 495 nm, 7 nm to 490 nm, 8 nm to 485 nm, 9 nm to 480 nm, 10 nm to 475 nm, 11 nm to 470 nm, 12 nm to 465 nm, 13 nm to 460 nm, 14 nm to 455 nm, 15 nm to 450 nm, 15 nm to 445 nm, 15 nm to 440 nm, 15 nm to 435 nm, 15 nm to 430 nm, 15 nm to 425 nm, 15 nm to 420 nm, 15 nm to 415 nm, 15 nm to 410 nm, 15 nm to 405 nm, 15 nm to 400 nm, 15 nm to 395 nm, 15 nm to 390 nm, 15 nm to 385 nm, 15 nm to 380 nm, 15 nm to 375 nm, 15 nm to 370 nm, 15 nm to 365 nm, 15 nm to 360 nm, 15 nm to 355 nm, 15 nm to 350 nm, 15 nm to 345 nm, 15 nm to 340 nm, 15 nm to 335 nm, 15 nm to 330 nm, 15 nm to 325 nm, 15 nm to 320 nm, 15 nm to 315 nm, 15 nm to 310 nm, 15 nm to 305 nm, or 15 nm to 300 nm.

In a fourth set of ranges, the inner diameter of the tip of a nanopipette probe is one of the following ranges: about 5 nm to 1µ, 15 nm to 365 nm, 16 nm to 350 nm, 17 nm to 325 nm, 18 nm to 315 nm, 19 nm to 305 nm, 20 nm to 295 nm, 21 nm to 285 nm, 22 nm to 275 nm, 23 nm to 265 nm, 24 nm to 255 nm, 25 nm to 250 nm, 20 nm to 250 nm, or 15 nm to 250 nm.

In some embodiments, an inner diameter of the tip is less than about 1µ (e.g., less than about 900 nm, 800 nm, 700 nm, 600 nm, 500 nm, or 400 nm). In further embodiments, an inner diameter of the tip is less than about 300 nm. In additional embodiments, an inner diameter of the tip is less than about 250 nm. In some embodiments, an inner diameter of the tip is between about 15 nm and about 40 nm. In other embodiments, an inner diameter of the tip is between about 20 nm and about 35 nm.

The inducing of an electrospray from a nanopipette in accordance with the present teachings includes providing a conductive liquid in the nanopipette, and applying a potential (e.g., between the conductive liquid and the substrate). While neither desiring to be bound by any particular theory nor intending to limit in any measure the scope of the appended claims or their equivalents, it is presently believed that if an applied potential is too low to induce an electrospray, a spike in current may result, which may cause damage to the nanopipette tip. In some embodiments, the applied potential is at least sufficiently large enough to induce the electrospray. In some embodiments, the applied potential is at least about 80 V. In other embodiments, the applied potential is between about 80 V and about 130 V. In some embodiments, the applied potential is about 50 V to about 200 V, about 80 V to about 200 V, about 80 V to about 150 V, about 80 V to about 120 V, about 80 V to about 110 V, about 80 V to about 100 V, about 90 V to about 200 V, about 90 V to about 150 V, about 90 V to about 120 V, about 90 V to about 110 V, about 100 V to about 200 V, about 100 V to about 150 V, or about 100 V to about 120 V.

All manner of conductive liquids, and combinations thereof, are contemplated for use in accordance with the present teachings. In some embodiments, the conductive liquid includes an electrolyte solution, including but not limited to an optionally buffered saline solution. In some embodiments, the conductive liquid includes a phosphate-buffered saline (PBS) solution. In some embodiments, the conductive liquid includes one or more charged inorganic and/or organic molecules. In some embodiments, the conductive liquid includes a charged monomer solution.

Substrates used in accordance with the present teachings may be connected to ground. In some embodiments, at least a portion of the substrate itself is conductive (e.g., a gold-coated glass slide or an agarose gel). In other embodiments, such as in Example 9 described below, the substrate itself is insulative (e.g., a polystyrene particle) but is proximal to a conductive material (e.g., an agarose gel).

In some embodiments, methods for imaging a substrate in accordance with the present teachings further include (d) recording a position of the nanopipette probe when the predefined electrospray current and/or distance threshold is reached. In other embodiments, methods for imaging a substrate in accordance with the present teachings include (d) recording a position of the nanopipette probe when the predefined electrospray current and/or distance threshold is reached, and further include one or more of (e) retracting the nanopipette probe (e.g., after the predefined electrospray current and/or distance threshold is reached); (f) advancing the nanopipette probe to a different lateral position relative to the surface of the substrate; and/or (g) repeating one or more of the above-described acts—including but not limited to the acts of (b) varying, (d) recording, (e) retracting, and/or (f) advancing—at one or a plurality of different lateral positions relative to the surface of the substrate.

In accordance with the present teachings, an electrospray emitted from a nanopipette probe may cause the deposition of material (e.g., salt from an electrolyte solution) onto the surface of a substrate. Salt deposited during imaging demonstrates the possibility of utilizing SESM as a tool for deposition and serves as a method to investigate the process of SESM, as further described below in reference to Example 8.

A method for spatially controlled deposition of material on a surface of a substrate in accordance with the present teachings includes: (i) introducing the material into a nanopipette probe; (ii) inducing an electrospray from the nanopipette probe, wherein the electrospray comprises the material; (iii) varying (e.g., decreasing and/or increasing) a distance between the nanopipette probe and the surface of the substrate until a predefined electrospray current and/or a predefined distance threshold is reached (e.g., at a single point on the surface of the substrate or at one or more of a plurality of points on the surface of the substrate); and (iv) retracting the nanopipette probe away from the surface of the substrate after the predefined electrospray current is reached at the respective point. In some embodiments, the method further includes (v) advancing the nanopipette probe to another point on the surface of the substrate and repeating one or more of the above-described acts, including but not limited to the acts of (iii) varying and/or (iv) retracting.

In some embodiments, a tip of the nanopipette probe used for depositing the material is less than about 300 nm. In other embodiments, a tip of the nanopipette probe used for depositing the material is between about 15 nm and about 250 nm. In some embodiments, the material deposited on the surface of the substrate includes a biomaterial, a polymer, a metal, an etching agent, or a combination thereof. While neither desiring to be bound by any particular theory nor intending to limit in any measure the scope of the appended claims or their equivalents, it is presently believed that the amount of material deposited on the surface of the substrate may be controlled through the rate at which the distance between the nanopipette probe and the surface of the substrate is varied and/or through the amount of potential applied to induce the electrospray.

Deposition of material as a consequence of the SESM imaging technique described herein may be used in a variety of applications, including but not limited to electrodeposition, micro-patterning, nano-patterning, nanofabrication, materials synthesis (e.g., electrospinning, electrospray deposition), semiconductor fabrication, and/or the like, and combinations thereof (see, for example: V. N. Morozov and T. Y. Morozova, *Anal. Chem.*, 1999, 71, 3110-3117; R. Moerman, J. Frank, J. C. M. Marijnissen, T. G. M. Schalkhammer and G. W. K. van Dedem, *Anal. Chem.*, 2001, 73, 2183-2189; K. Kim, B. U. Lee, G. B. Hwang, J. H. Lee and S. Kim, *Anal. Chem.*, 2010, 82, 2109-2112; J. Kameoka, R. Orth, Y. Yang, D. Czaplewski, R. Mathers, G. W. Coates and H. G. Craighead, *Nanotechnology*, 2003, 14, 1124-1129; F. Iwata, S. Nagami, Y. Sumiya and A. Sasaki, *Nanotechnology*, 2007, 18, 105301; and S. Ito, T. Keino and F. Iwata, *Jpn. J. Appl. Phys.*, 2010, 49, 08LB16).

In accordance with the present teachings, distance-dependent electrospray from nanopipettes may be used to provide signals for topographic imaging. As further described in the Examples below, approach curves have experimentally demonstrated the relationship between electrospray current and distance between the probe and substrate. Approach-retract scanning (ARS) mode may be utilized to generate an image of both insulative and conductive topographical features.

In addition, in some embodiments, SESM as an imaging method may be used in tandem with ambient mass spectrometry imaging (MSI). SESM may be integrated with MS in a desorption electrospray ionization (DESI) mass spectrometry imaging format. Nanopipettes are smaller than conventional DESI emitters, and may be used to lower the spot size of analysis. Sampling from a smaller surface area may also increase spatial resolution (although smaller spot sizes may limit the overall MS signal). Additionally, SESM may be used to add dynamic probe-distance control and topographic imaging to MSI.

The following examples and representative procedures illustrate features in accordance with the present teachings, and are provided solely by way of illustration. They are not intended to limit the scope of the appended claims or their equivalents.

EXAMPLES

Example 1: Materials

A solution of 1× phosphate-buffered saline (PBS) was prepared with 18 MΩ·cm $H_2O$ from a Milli-Q water purification system (EMD Millipore, Billerica, Mass.) and used as a spray solvent. Agarose solutions (5% w/v) were prepared from molecular grade agarose (Bioline, Taunton, Mass.) with 1×PBS as the solvent. Ultra fine square 1500 mesh TEM grids (G1500HS, Ted Pella, Redding, Calif.) with 11.5 μm wide holes, 5 μm wide bars were used to prepare a topographical feature for imaging. Polystyrene microspheres (Polyspherex™ PS-COOH) with an average diameter of 3 μm were obtained from Phosporex, Inc. (Hopkinton, Mass.) and were used as an insulative topographical feature.

Example 2: Nanopipette Fabrication and Characterization

A P-2000 $CO_2$ laser puller (Sutter Instrument, Novato, Calif.) was used to pull quartz capillaries (Q100-70-7.5, Sutter Instrument, Novato, Calif.) to inner diameters that range from 20 nm to 35 nm. All capillaries were cleaned with piranha solution (3:1 v/v $H_2SO_4$:30% $H_2O_2$) prior to pulling. After fabrication, all pipettes were imaged using scanning electron microscopy and scanning transmission electron microscopy (Quanta FEG 600F, FEI, Hillsboro, Oreg.). Pipettes were back-filled with PBS using a MicroFil needle (World Precision Instruments, Sarasota, Fla.) and centrifuged before use in experiments.

Example 3: Substrate Preparation

For approach curve experiments, either a gold-coated glass slide or an agarose gel was prepared as a substrate. Glass slides were prepared with a 10 nm chromium adhesion layer, followed by an 80 nm gold layer using a thermal evaporator (BOC Edwards, Auto 306 Vacuum Coater, West Sussex, United Kingdom).

To prepare the agarose substrate for both approach curves and for imaging, an agarose solution (5% w/v in 1×PBS) was heated until boiling and cast onto a TEM grid. After gelling, the TEM grid was peeled from the agarose gel, which was prepared for imaging. For experiments, the agarose gel was placed on a gold-coated glass slide, which had a copper contact pad to attach to a grounded electrode. Approach curves were performed over a flat area on the gel, while imaging was performed over the negative of the TEM topographical features. To prepare an insulative feature for imaging, polystyrene microspheres were drop-cast onto the agarose gel. Agarose casts were stored in 1×PBS buffer when not in use, to ensure the gel stayed hydrated.

Example 4: General Procedure for SESM

Nanopipette probes were pulled to inner diameters between 20 nm and 35 nm. Probe size and integrity were characterized by electron microscopy before and after experiments. Pipettes were backfilled with 1×PBS and subsequently mounted in a holder which included a back-inserted Pt wire for application of potential.

A commercial scanning ion conductance microscope (Park Systems XE-Bio SICM/AFM, Suwon, South Korea) was used to control probe position. An external power supply (Keithley 6487, Cleveland, Ohio) was used to bias the probe tip at potentials sufficient to result in electrospray. For SESM experiments, at relevant distances, the electrospray current increases as the probe-surface distance ($D_{PS}$) decreases. Distance-dependence of the current is the opposite of the case for SICM, where currents decrease as the probe moves toward the surface. To account for this instrumentally, custom electronics were employed to invert the electrospray signal such that it could be fed into the commercial SICM. The current inverter allowed utilization of approach curves, approach-retract scanning (ARS) (T. Ushiki, M. Nakajima, M. Choi, S.-J. Cho and F. Iwata, *Micron*, 2012, 43, 1390-1398) and other instrument protocols available in the SICM software/controller. Substrates examined were connected to ground, and included gold-coated glass slides or agarose gels. A bias between +80 and +130V was applied to the pipette electrode to induce electrospray.

Example 5: SESM Approach and Imaging Parameters

For approach curves, pipettes were approached at a rate of 0.3 µm/s until reaching a current limit of either 25 nA spray current (on gold-coated glass slide) or 35 nA spray current (on agarose gel).

SESM was used to image topographical features, as well as to deposit salt on the substrate surface for characterization of the SESM process. Approach-retract scanning parameters are shown in Table 1. For salt deposit characterization, fewer pixels were used in comparison to topographical imaging, and 8×8 pixels were acquired over a 75 µm×75 µm area on a flat, gold-coated glass slide. For all imaging experiments, the probe was first approached to the surface and an appropriate current range was achieved by tuning the applied potential, which varied slightly between pipettes.

TABLE 1

Figure 5:
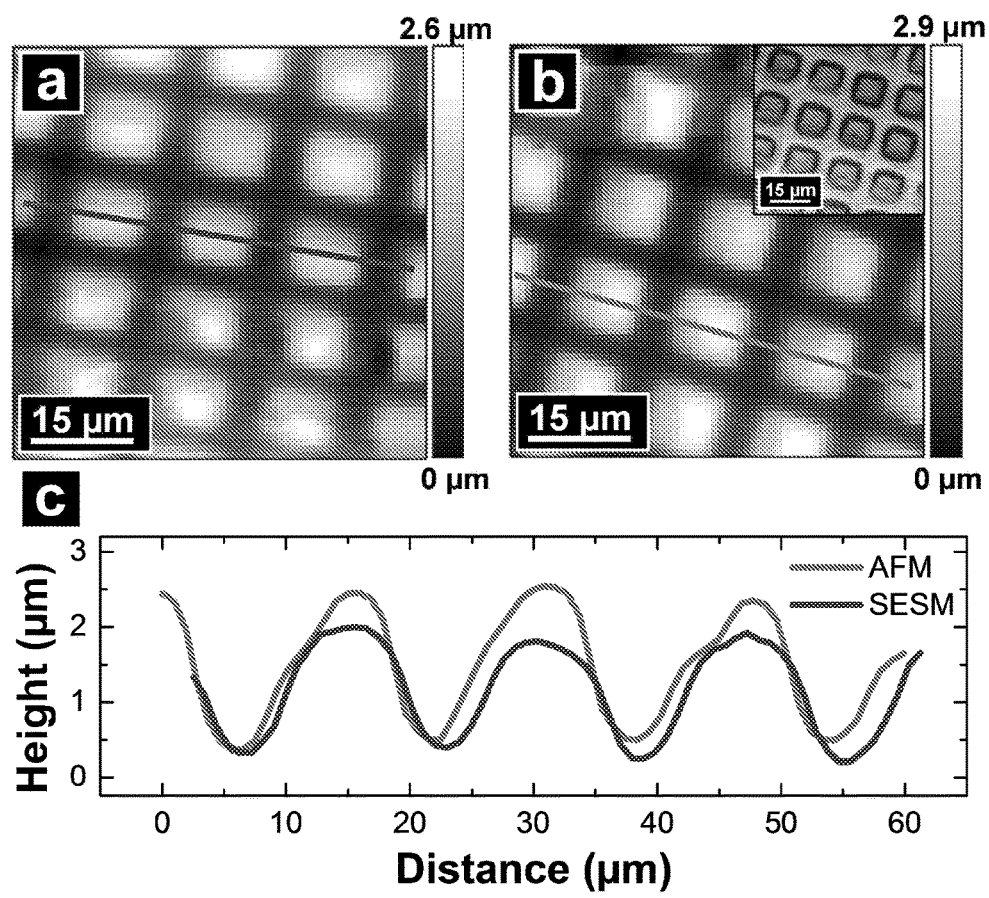
FIG. 5a shows a scanning electrospray microscopy (SESM) image of an agarose gel replica (negative) of a transmission electron microscopy (TEM) grid.
FIG. 5b shows an atomic force microscopy (AFM) image of the agarose gel replica (negative) of the TEM grid. The inset in FIG. 5b shows an optical image of the substrate.
FIG. 5c shows a comparison of the line scans from the SESM and AFM images.
Figure 6:
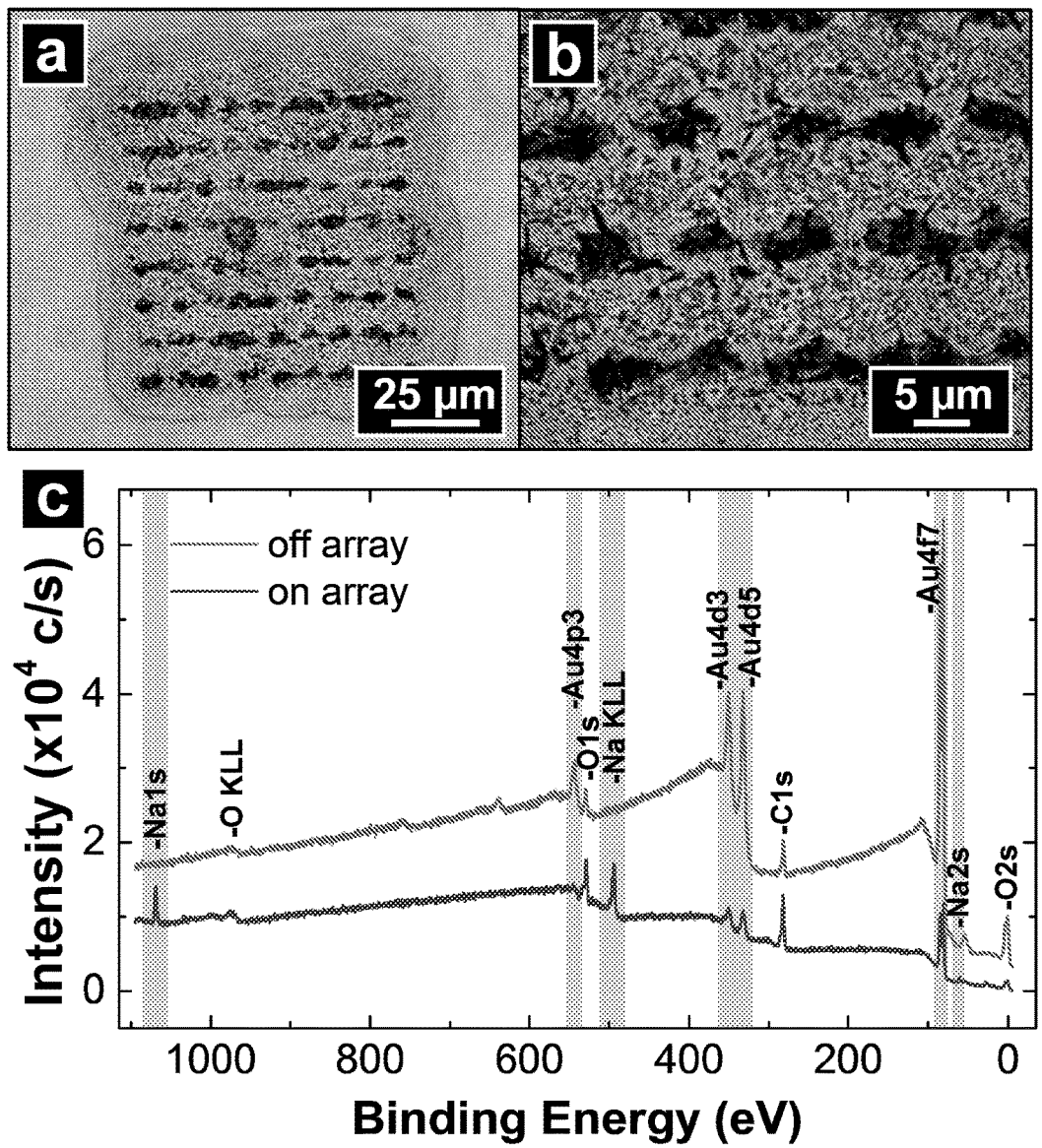
Figure 7:
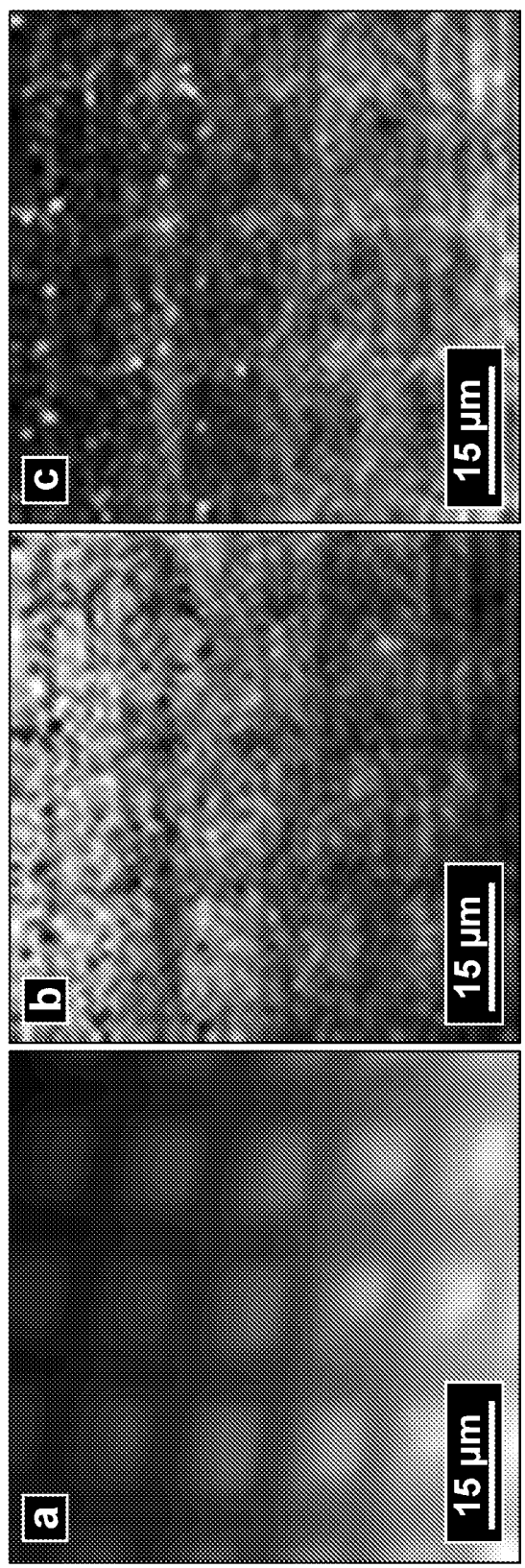
FIGS. 7a, 7b, and 7c show, respectively, raw topography, current, and error images for the SESM image shown in FIG. 5.
Figure 9:
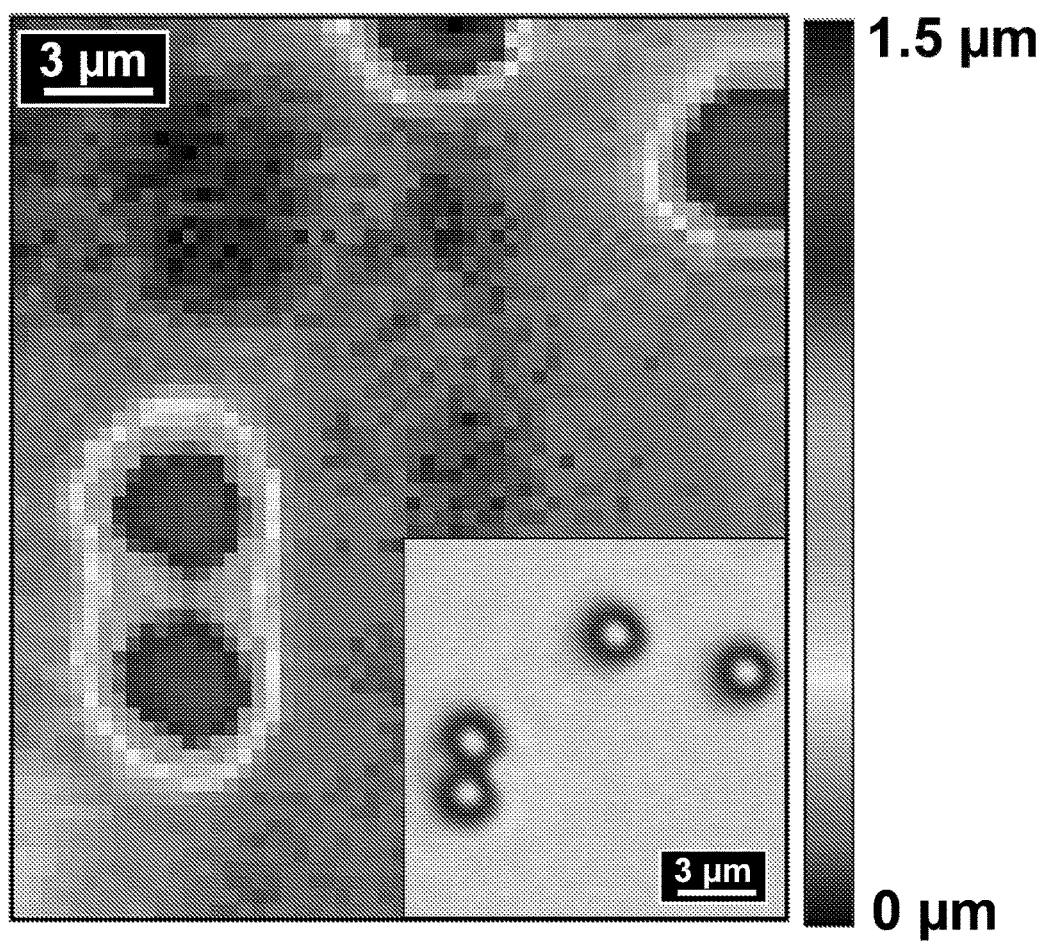
FIG. 9 shows a SESM image of 3 μm-diameter polystyrene particles on an agarose substrate. The inset in FIG. 9 shows an optical image of the same region of polystyrene particles.

Approach-retract scanning mode imaging parameters for SESM imaging (seen in FIGS. 5 and 9) and for salt deposition studies (seen in FIG. 6)

| Parameter | SESM Imaging | Salt Deposition |
|---|---|---|
| Retract height (µm) | 0.5-1.5 | 1.5 |
| Retract step size (µm) | 0.05 | 0.05 |
| Course approach rate (µm/s) | 0.006 | 0.006 |
| Fine approach rate (µm/s) | 0.001 | 0.001 |
| Current minimum (nA) | 1 | 1 |
| Current maximum (nA) | 7 | 7 |
| Current threshold (%) | 5 | 5 |
| Current average | 3x | 3x |
| Lift during XY offset (µm) | 1.5-2.0 | 2.5 |
| Overall delay (µs) | 0 | 100 |
| XY move delay (µs) | 20 | 100 |
| Pre-approach delay (µs) | 100 | 100 |
| Pixel number | 64 × 64 | 8 × 8 |

AFM Conditions: An XE-Bio SICM/AFM by Park Instruments was used to acquire an image of the agarose TEM grid replica in non-contact mode. An NCHR cantilever from Nanoworld was used (Neuchâtel, Switzerland) and a scan rate of 0.3 Hz was applied with a set point of 20.0 nm.

XPS Parameters: X-ray photoelectron spectroscopy experiments were carried out using a PHI Versa Probe II (Physical Electronics, Hanhassen, Minn.) instrument equipped with a monochromatic Al Kα focused source. Instrument base pressure was ca. $8 \times 10^{-10}$ Torr. The 50 µm beam at 12.5 W and 15 kV was used for spectral acquisition at the X-ray incidence and take off angle of 45°. The instrument work function was calibrated to give a binding energy (BE) of 84.0 eV for Au $4f_{7/2}$ line for metallic gold and the spectrometer dispersion was adjusted to give BEs of 284.8 eV and of 368.3 eV for the C is line of adventitious (aliphatic) carbon presented on the non-sputtered samples, Cu $2p_{3/2}$ and Ag $3d_{5/2}$ photoemission lines, respectively. The PHI dual charge compensation system was used on all samples. Spectra were acquired over a spot directly on a deposited array and on an area of clean gold. Data was averaged over 5 cycles, with 3 sweeps/cycle. The ultimate Versa Probe II instrumental resolution was determined to be better than 0.125 eV using the Fermi edge of the valence band for metallic silver. All XPS spectra were recorded using PHI software SmartSoft—XPS v2.0 and processed using PHI Multipak v9.0.

For mapping experiments (FIG. 9), a 9.0 µm beam at 1.0 W and 15 kV was used at an X-ray incidence and take off angle of 45°. Maps were collected over a 350×350 µm area at 256×256 pixels. For the Na1s map, 20 frames were acquired, while 5 frames were collected for the Au4f map.

Example 6: Approach Curves

Figure 2:
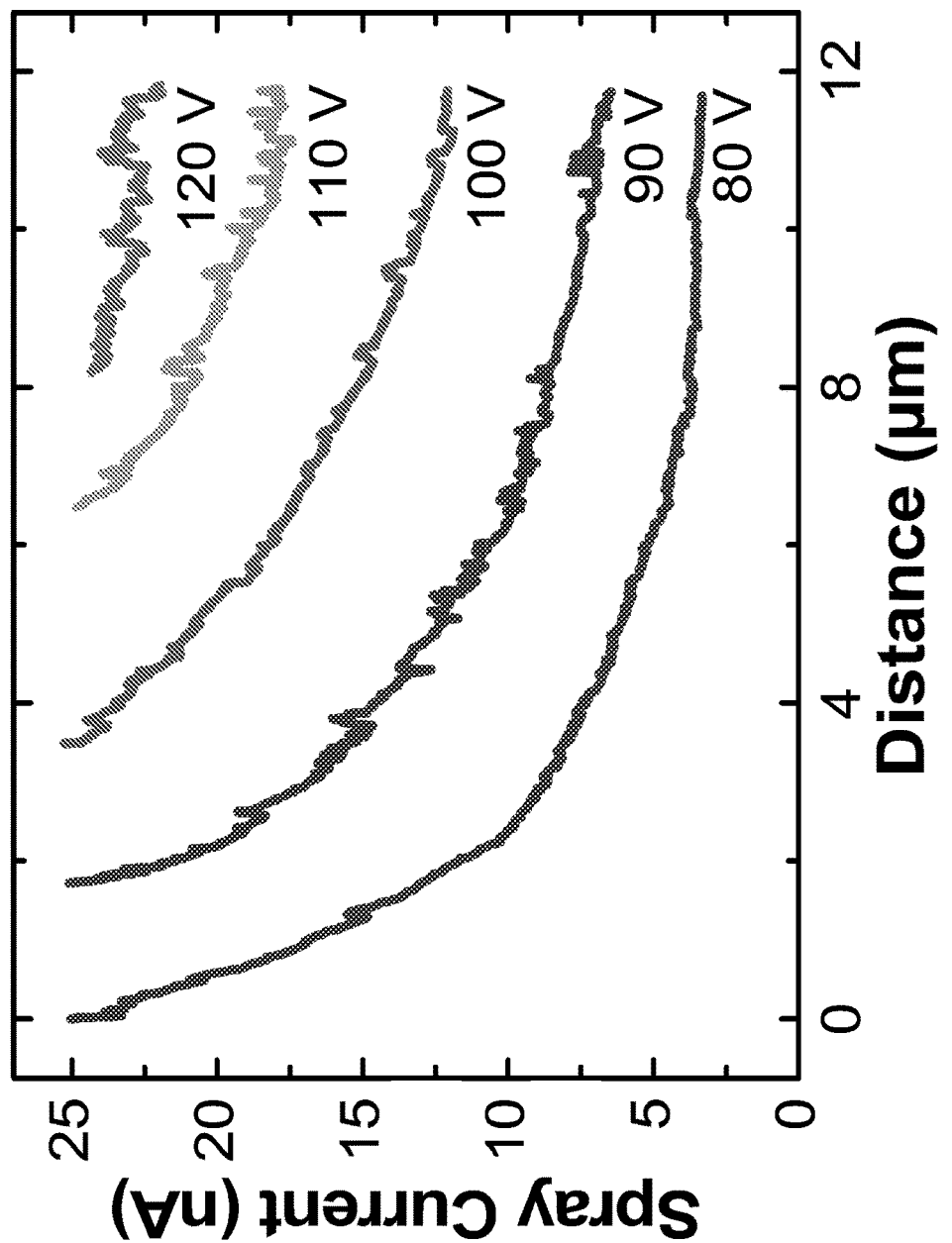
FIG. 2 shows representative approach curves obtained over a gold-coated glass slide at 80, 90, 100, 110, and 120V with a nanopipette having an inner diameter (i.d.) of about 22 nm.

Approach curves as shown in FIG. 2 were measured to characterize the current-distance relationship experimentally. For example, in a typical approach curve, 100 V was applied to the pipette electrode while the pipette was held over a gold substrate. As the probe approached the surface, electrospray current between the probe tip and substrate was observed, typically at distances tens of microns from the surface. The probe-surface distance was decreased further until either a predetermined distance or a current set point (chosen arbitrarily as 25 nA spray current, as shown in FIG. 2) was met. The general shape of experimental approach curves agrees with a distance-dependent relationship similar to what EQN. (3) predicts. A plateau region is seen at large $D_{PS}$, and electrospray current remains relatively constant as $D_{PS}$ is initially decreased. As $D_{PS}$ decreases further, a sharp increase in spray current is observed. Although the general trend holds, fitting of approach curves with the explicit relationship in EQNS. (1)-(3) was unsuccessful. While neither desiring to be bound by any particular theory nor intending to limit in any measure the scope of the appended claims or their equivalents, it is presently believed that the failure originates from the difference in tip dimensions (micro vs. nano) used in the original derivations of equations and in experiments here. At nanoscale dimensions, the influence of parameters such as surface tension may cause a deviation from the relationship shown (Y. T. Cheng, D. E. Rodak, C. A. Wong and C. A. Hayden, *Nanotechnology*, 2006, 17, 1359-1362; T.-S. Wong and C.-M. Ho, *Langmuir*, 2009, 25, 12851-12854).

Multiple approach curves shown in FIG. 2 were recorded over a range of potentials (80 V through 120 V) with the same pipette. Potentials lower than 80 V often did not induce electrospray (perhaps due to insufficient electric fields to support electrospray). If no electrospray was induced, an immediate spike in current resulted, which often broke the pipette tip (in the case of gold surfaces), rather than the gradual increase observed for approaches illustrated in FIG. 2. Approach curves generally followed the same trend (e.g., a nonlinear, fast rising increase at decreased probe-surface distances). As applied potential increased, higher spray currents were observed at similar probe-surface distances, and the onset of the current rise was recorded further from the surface, as compared to approaches at lower applied potentials.

Figure 3:
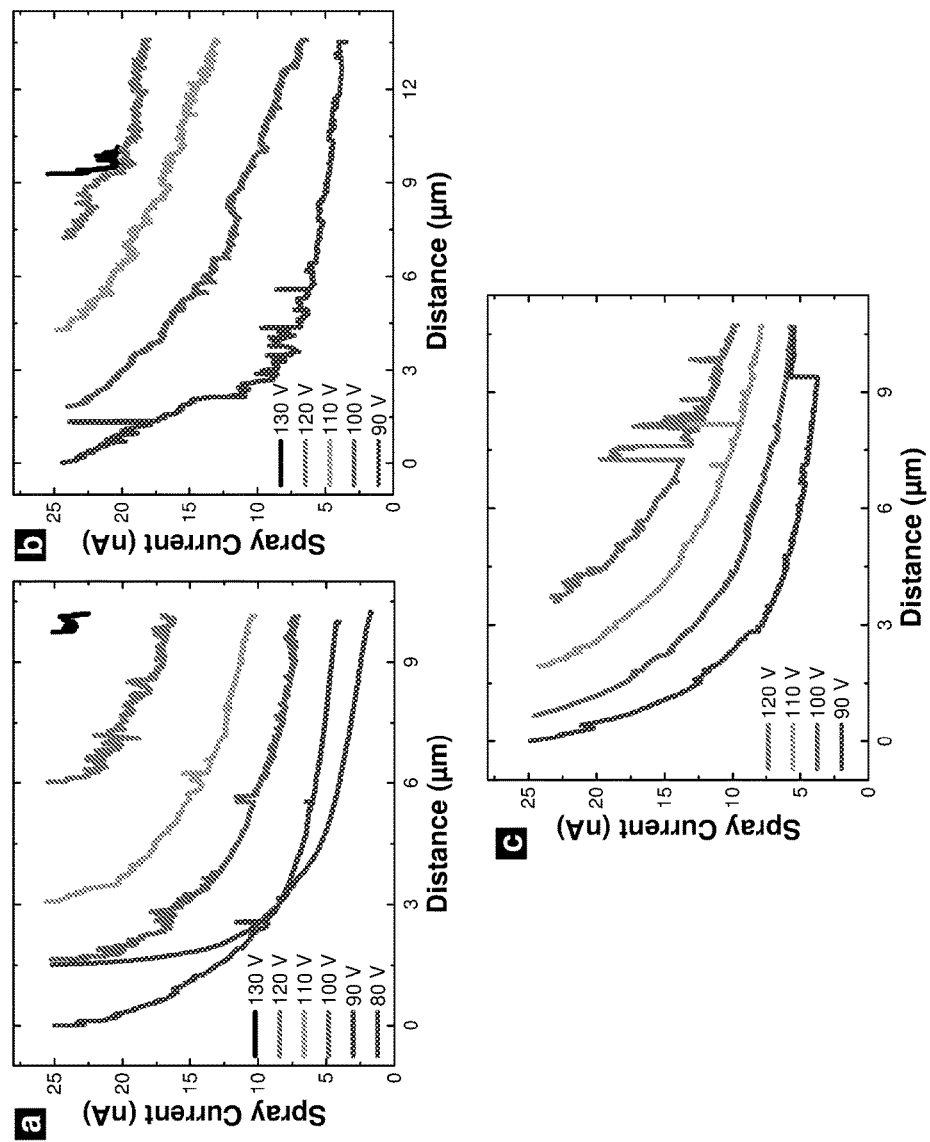
FIGS. 3a, 3b, and 3c show additional representative approach curves obtained over a gold-coated substrate with a nanopipette having an inner diameter (i.d.) of about 35 nm.
Figure 4:
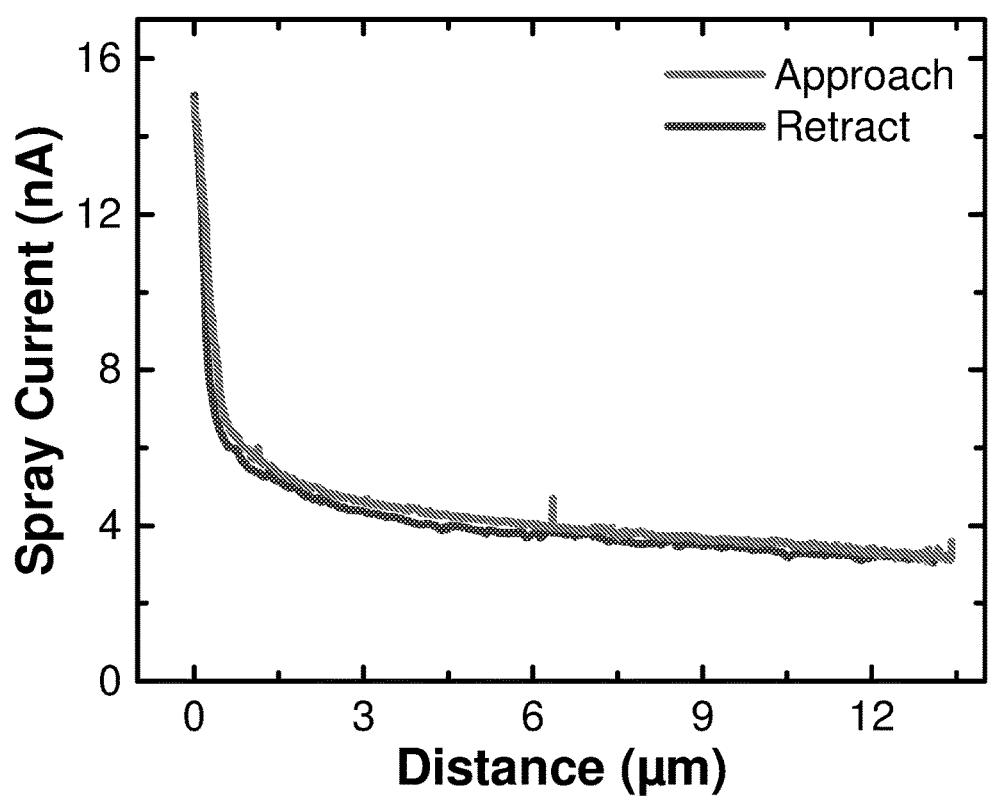
FIG. 4 shows representative approach and retract curves obtained over an agarose substrate at an applied potential of 100 V with a nanopipette having an inner diameter of about 22 nm (before and after).

Despite similar pipette inner diameters, approach curves varied to some degree for different pipettes as shown in FIG. 3. However the overall shape of the approach curve was maintained, which suggests that pipette geometry (and the resulting effects on electric field) may influence the exact current-distance relationship. Due to slight variations between different pipettes in the current-distance response, applied potentials were optimized for each pipette prior to imaging, but typically fell between 80 V and 100 V. Approach and retract curves were also recorded on agarose, as shown in FIG. 4, and had good agreement with minimal hysteresis, indicative of a robust current-distance relationship. The compliant nature of agarose gels generally provided a more forgiving surface for repeated approach-retract cycles. Nanopipette dimensions were monitored by SEM and scanning transmission electron microscopy (STEM) to verify that tips survived approach curves and the electrospray process (e.g., about 22 nm i.d. before and after approaching for FIG. 4).

Choice of applied potential is related to the imaging distance and subsequent resolution. For the current range investigated here, approach curves recorded at the lowest potentials demonstrated the sharpest increase in current with decreasing probe-surface distance, as shown in FIG. 2. For data shown in FIG. 2, an x-offset was observed between each approach curve. This x-offset arises from the differences in applied potential and the nature of the experiment. Approaches were performed sequentially from lowest to highest applied potential over the same position on the substrate to prevent any effects from surface tilt. As a result of the electrospray mechanism employed in SESM, salt is deposited on the substrate surface. Thus, for data shown, subsequent approach curves over the same spot then occur on top of the deposited salt, which may result in a net effect of smaller DPS. Thus, sequential approach curves (such as those shown in FIG. 2) taken at the same position have an increasingly positive x-offset. To illustrate this effect, FIG. 3a (ESI) shows a set of approaches that were started at 90 V and increased to 130 V applied potential before returning to an 80 V applied potential. While the shape of the 80 V approach here is sharper than curves for higher potentials and more similar to the lower potential approaches in FIG. 2, the x-offset is increased, which suggests that a salt buildup on the surface may contribute to x-offset between approaches.

Example 7: SESM for Imaging Topography of a Conductive Surface

SESM was used to image an agarose mold cast from a transmission electron microscopy (TEM) grid. An SESM image of the mold, along with an atomic force microscopy (AFM) image and an optical image are shown, respectively, in FIG. 5a, FIG. 5b, and FIG. 5b inset. A 60 μm×60 μm area was imaged at 64×64 pixels for both SESM and AFM. For SESM, 90 V was applied to the pipette electrode and a set point of 2.5 nA was used for ARS imaging. In the SESM image shown in FIG. 5a, the agarose mold is reproduced with fidelity. Dimensions of the TEM grid (center hole and bar dimensions), which correspond to pillars and spacing between pillars in the agarose mold, are 11.5 μm and 5 μm, respectively, as compared to 10.7±1.1 μm (n=9) and 3.9±1.0 μm (n=9) in the SESM image. SEM images showed the pipette size was about 25 nm i.d. after imaging, as compared to 22 nm i.d. before experiments, which indicates the pipette remained intact throughout imaging. In FIG. 5c, line scans over the images in FIGS. 5a and 5b show that SESM measures similar feature depths as AFM (SESM about 1.5 μm, as compared to 2.0 μm for AFM).

Example 8: SESM for Spatially Controlled Deposition of Material

Salt deposited during imaging demonstrates the possibility of utilizing SESM as a tool for deposition and serves as a method to investigate the process of SESM. To characterize deposited salt, a pipette was used to image a flat gold-coated surface in ARS mode. SEM, XPS, and XPS mapping were then performed for the area imaged by SESM. Deposits were made by spraying 1×PBS solution at 8×8 pixel spacing over a 75 μm×75 μm area. Salt deposition is observed at each pixel, as shown in FIGS. 6a and 6b, and was 4.44±0.72 μm in diameter (n=13 measurements). Image size and the number of pixels give an expected spacing between deposits of 9.38 μm. Spacing between deposited spots was slightly larger in the y-axis (10.64±0.58 μm, n=11) than the fast-scan x-axis (9.51±0.68 μm, n=11). In the fast-scan axis, individual spots deposited are not always well resolved, which suggests solvent did not completely evaporate during spray, or that spray did not fully turn off when translating in the x-direction to the next pixel location.

Figure 8:
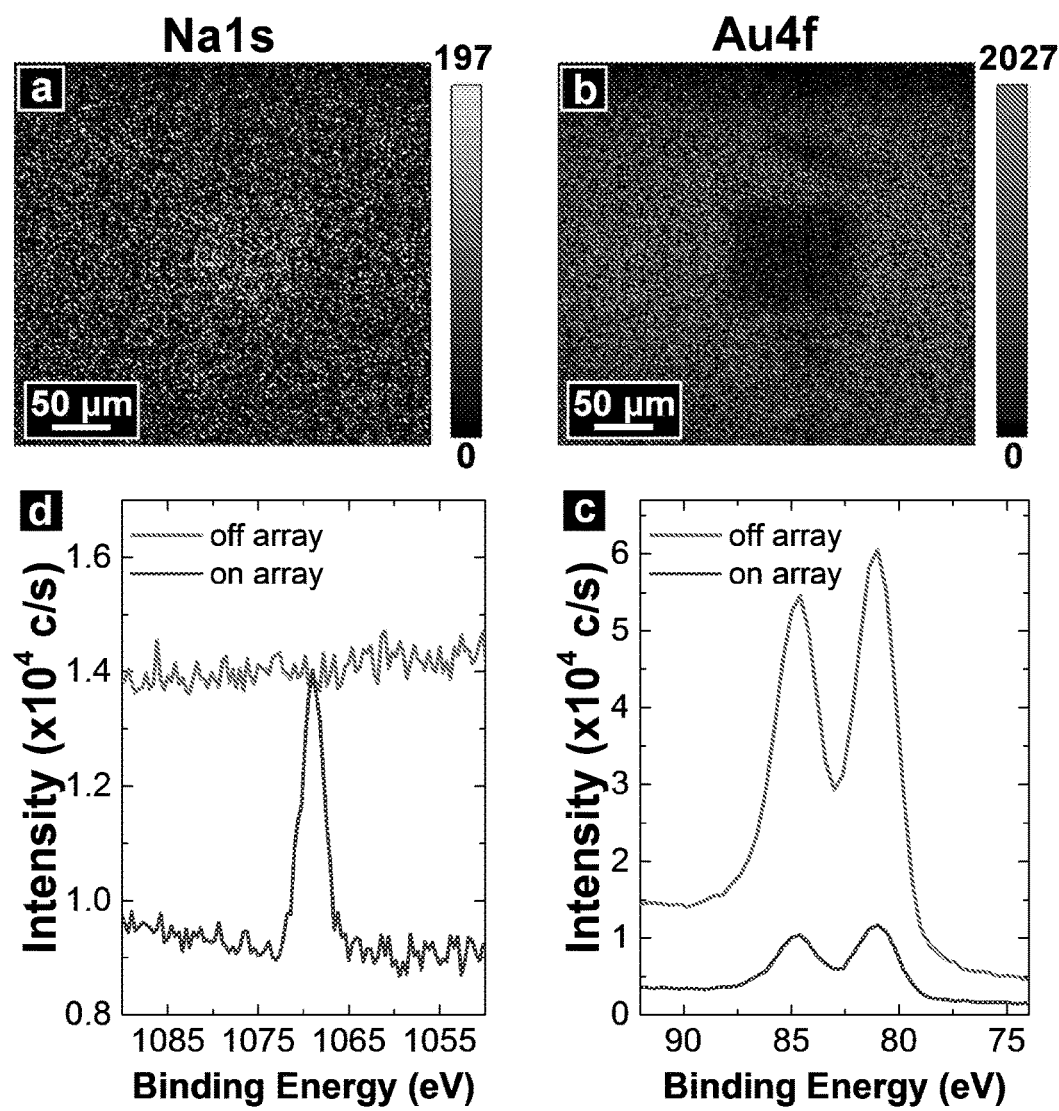
FIG. 8a shows a Na1s map of a salt deposited area.
FIG. 8b shows an Au4f XPS map of a salt deposited area.
FIG. 8c shows a zoomed-in area of Na1s peak comparison on an XPS survey scan.
FIG. 8d shows a zoomed-in area of Au4f peak comparison on an XPS survey scan.

XPS and XPS mapping were used to characterize deposits left on the sample from SESM, as shown by FIG. 6c and FIG. 8, respectively. In the XPS spectra, peaks for sodium (Na1s, Na KLL, and Na2s) appear over the imaged area, while the same peaks are absent in areas not imaged by SESM. Signals from gold are attenuated for XPS on the area imaged by SESM as compared to areas that were not imaged. Since XPS analysis is surface-sensitive, the salt deposits from SESM attenuate the gold signal. Salt deposits from 1×PBS are shown. However when alternative solutions are used, SESM provides a tool for spatially controlled deposition of biomaterials, polymers, or metals. Approach rate and applied potential may be used to control the amount of material deposited.

Example 9: SESM for Imaging Topography of an Insulative Surface

Figure 10:
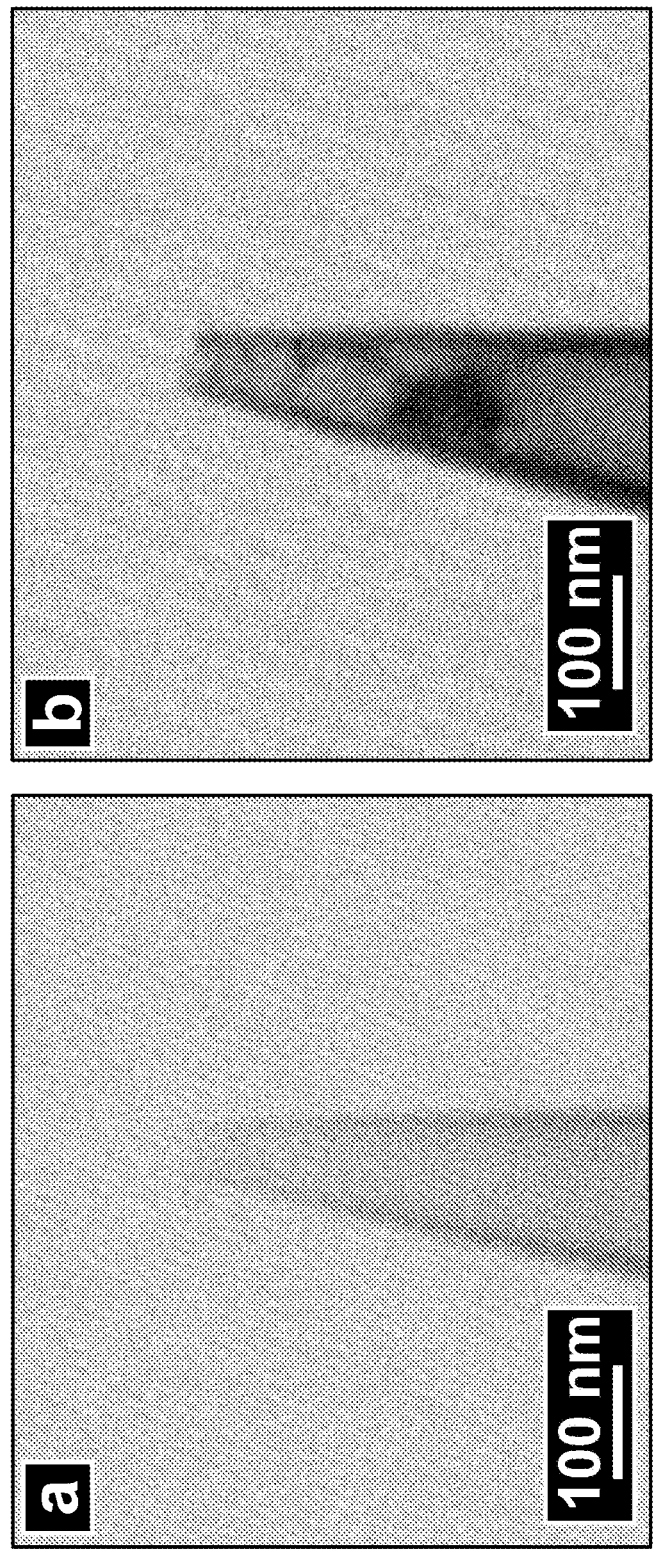
FIGS. 10a and 10b show, respectively, scanning transmission electron microscopy (STEM) images of a pipette before and after obtaining the SESM image in FIG. 9. The inner diameter of the nanopipette before imaging was about 30 nm compared to about 35 nm after imaging.

Insulating features on top of a conductive substrate may also be imaged with SESM. Imaging of polystyrene microspheres on an agarose substrate produced the topographical image shown in FIG. 9. Vertical resolution is not representative of the true particle size (seen in attenuation of the particle height, about 1.4 μm vs. the 3 μm mean diameter from the manufacturer), which may be due to the lower conductivity over the particles. However, lateral resolution appears to be consistent with accepted particle size (3.3±0.2 μm in particle diameter, n=5 measurements). Pipette geometry and size were maintained before and after imaging, as shown in FIG. 10. These results suggest that with probe-surface distances that are relatively large (e.g., low current set point, high $D_{PS}$), the electric field from the conductive agarose gel underneath and surrounding the particles is sufficient to maintain electrospray. Thus, while SESM may use a conductive substrate in some examples, lateral resolution when imaging insulative features on top of a conductive substrate may be maintained.

The entire contents of each and every patent and non-patent publication cited herein are hereby incorporated by reference, except that in the event of any inconsistent disclosure or definition from the present specification, the disclosure or definition herein shall be deemed to prevail.

It is to be understood that use of the indefinite articles "a" and "an" in reference to an element does not exclude the presence, in some embodiments, of a plurality of such elements.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method for imaging a substrate, the method comprising:
   inducing an electrospray from a nanopipette probe;
   varying a distance between the nanopipette probe and a surface of the substrate until a predefined electrospray current and/or a predefined distance threshold is reached; and
   determining a topography of the surface of the substrate based on feedback derived from distance dependency of the electrospray current.

2. The method of claim 1 wherein the electrospray current increases as the distance decreases.

3. The method of claim 1 wherein an inner diameter of a tip of the nanopipette probe is less than about 300 nm.

4. The method of claim 1 wherein an inner diameter of a tip of the nanopipette probe is between about 15 nm and about 250 nm.

5. The method of claim 1 wherein the inducing comprises:
   providing a conductive liquid in the nanopipette; and
   applying a potential between the conductive liquid and the substrate.

6. The method of claim 5 wherein the potential is large enough to induce the electrospray.

7. The method of claim 5 wherein the conductive liquid comprises an electrolyte solution, a charged monomer solution, or a combination thereof.

8. The method of claim 5 wherein at least a portion of the substrate is conductive.

9. The method of claim 5 wherein the substrate is insulative and proximal to a conductive material.

10. The method of claim 1 further comprising recording a position of the nanopipette probe when the predefined electrospray current is reached.

11. The method of claim 1 further comprising:
    recording a position of the nanopipette probe when the predefined electrospray current is reached;
    retracting the nanopipette probe after the predefined electrospray current is reached;
    advancing the nanopipette probe to a different lateral position relative to the surface of the substrate; and
    repeating the varying and the recording at the different lateral position.

12. A method for imaging a substrate via scanning electrospray microscopy, the method comprising:
    inducing an electrospray from a nanopipette probe, wherein an inner diameter of a tip of the nanopipette probe is less than about 300 nm;
    scanning the substrate with the nanopipette probe at each of a plurality of lateral points relative to a surface of the substrate;
    decreasing distance between the nanopipette probe and the surface of the substrate until a predefined electrospray current threshold is reached;
    recording a position of the nanopipette probe when the predefined electrospray current threshold is reached; and
    determining a topography of the surface of the substrate based on feedback derived from distance dependency of electrospray current.

13. An apparatus for performing scanning electrospray microscopy, the apparatus comprising:
    a nanopipette probe movably mounted relative to a surface of a substrate, wherein the nanopipette probe is configured to emit an electrospray;
    an electrode provided in the nanopipette probe;
    a counter-electrode provided on or proximal to the surface of the substrate;
    a power source configured to induce a potential between the electrode and the surface sufficient to induce an electrospray directed towards the surface of the substrate;
    a current monitoring unit configured to measure an electrospray current; and
    a computer processor coupled to a non-transitory memory, wherein the computer processor is operative to execute computer program instructions to cause the processor to determine a topography of the surface of the substrate based on feedback derived from distance dependency of electrospray current.

14. The apparatus of claim 13 further comprising:
    a piezoelectric motor configured to raise, lower, and/or laterally translate a position of the nanopipette probe relative to the surface of the substrate.

15. The apparatus of claim 13 further comprising:
    a conductive liquid provided in an interior of the nanopipette probe in contact with the electrode.

16. The apparatus of claim 15 wherein the conductive liquid comprises an electrolyte solution, a charged monomer solution, or a combination thereof.

17. A method for spatially controlled deposition of material on a surface of a substrate, the method comprising:
    introducing the material into a nanopipette;
    inducing an electrospray from the nanopipette, wherein the electrospray comprises the material; and
    decreasing a distance between the nanopipette and the surface of the substrate until a predefined electrospray current and/or a predefined distance threshold is reached at the surface of the substrate.

18. The method of claim 17 wherein a tip of the nanopipette is less than about 300 nm.

19. The method of claim 17 wherein the material comprises a biomaterial, a polymer, a metal, or an etching agent.

20. The method of claim 17 further comprising controlling an amount of the material deposited on the surface of the substrate through a rate of the decreasing and/or an amount of potential applied to induce the electro spray.

* * * * *